United States Patent
Binder et al.

(10) Patent No.: US 10,569,195 B2
(45) Date of Patent: Feb. 25, 2020

(54) METHOD FOR ADJUSTING THE COMPOSITION OF CHROMATOGRAPHY PRODUCTS

(71) Applicant: Archer Daniels Midland Company, Decatur, IL (US)

(72) Inventors: Thomas Binder, Marion, IA (US); Mitchell J. Schultz, Decatur, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 375 days.

(21) Appl. No.: 15/518,278

(22) PCT Filed: Oct. 13, 2015

(86) PCT No.: PCT/US2015/055224
§ 371 (c)(1),
(2) Date: Apr. 11, 2017

(87) PCT Pub. No.: WO2016/061037
PCT Pub. Date: Apr. 21, 2016

(65) Prior Publication Data
US 2017/0304745 A1 Oct. 26, 2017

Related U.S. Application Data

(60) Provisional application No. 62/063,476, filed on Oct. 14, 2014.

(51) Int. Cl.
*B01D 15/18* (2006.01)
*B01D 15/36* (2006.01)
(Continued)

(52) U.S. Cl.
CPC ....... *B01D 15/1828* (2013.01); *B01D 15/185* (2013.01); *B01D 15/362* (2013.01);
(Continued)

(58) Field of Classification Search
CPC .. B01D 15/18; B01D 15/185; B01D 15/1828; B01D 15/362; B01D 15/128;
(Continued)

(56) References Cited

U.S. PATENT DOCUMENTS 4,373,025 A * 2/1983 Neuzil .................. C07H 1/06
127/46.1
4,412,866 A * 11/1983 Schoenrock ....... B01D 15/1828
127/46.2

(Continued)

*Primary Examiner* — Benjamin L Lebron
(74) *Attorney, Agent, or Firm* — Andrew F. Nilles (57) ABSTRACT

Described herein is a method of adjusting the composition of a chromatography product to achieve a target enriched proportion of a desired component from an input feed having a lower proportion of the desired component using simulated moving bed ("SMB") chromatography wherein the eluent for the SMB apparatus may comprise the very input feed being enriched. The method is exemplified by enriching a high fructose corn syrup from a 42% fructose syrup to a 55% fructose syrup without substantially reducing the dissolved solids concentration of the 55% syrup relative to the input 42% syrup. The 42% syrup is also used as the eluent for the SMB apparatus and may be reconstituted from the raffinate stream by passing the raffinate stream over a glucose isomerase column alone or in combination with a dextrose feed. The method reduces water usage and saves energy by minimizing the need for evaporation to obtain a 55% fructose syrup with a high dissolved solids content.

19 Claims, 10 Drawing Sheets

(51) Int. Cl.

| | |
|---|---|
| *B01J 39/26* | (2006.01) |
| *C07H 1/06* | (2006.01) |
| *C13B 20/14* | (2011.01) |
| *C13K 1/08* | (2006.01) |
| *C13K 3/00* | (2006.01) |
| *C13K 11/00* | (2006.01) |

(52) U.S. Cl.
 CPC ............... *B01J 39/26* (2013.01); *C07H 1/06* (2013.01); *C13B 20/148* (2013.01); *C13K 1/08* (2013.01); *C13K 3/00* (2013.01); *C13K 11/00* (2013.01); *B01D 15/1842* (2013.01); *B01D 2215/023* (2013.01)

(58) Field of Classification Search
 CPC .......... B01D 15/1842; B01D 2215/023; C13K 1/08; C13K 3/00; C13K 11/00; B01J 39/26; C07H 1/06; C13B 20/148
 See application file for complete search history.

(56) References Cited

U.S. PATENT DOCUMENTS

| | | | | |
|---|---|---|---|---|
| 6,224,776 | B1* | 5/2001 | Heikkila | B01D 15/1828 127/46.2 |
| 6,299,694 | B1* | 10/2001 | Ma | C13B 20/144 127/46.2 |
| 6,479,700 | B2* | 11/2002 | Soper | C07C 227/40 562/553 |
| 6,602,420 | B2* | 8/2003 | Kearney | B01D 15/1828 127/46.2 |
| 6,896,811 | B2* | 5/2005 | Heikkila | B01D 15/1828 127/46.2 |
| 6,896,812 | B1* | 5/2005 | Frey | B01D 15/1828 210/198.2 |
| 7,931,751 | B2* | 4/2011 | Costesso | B01D 15/1821 127/46.2 |
| 2010/0212662 | A1* | 8/2010 | Airaksinen | B01D 15/185 127/42 |

* cited by examiner

| date | | ~125% plant resin utilization | | | ~200% plant resin utilization | | |
|---|---|---|---|---|---|---|---|
| | | 2/27/2013 | 3/5/2013 | 3/28/2013 | 5/18/2013 | 7/6/2013 | 5/16/2013 |
| resin | UB8SSS-Ca | | | | | | |
| geometry | elution-enrich-feed-reload | 2-3-3-0 | 2-3-3-0 | 2-3-3-0 | 2-3-3-0 | 2-3-3-0 | 2-3-3-0 |
| total resin volume | mL | 1200 | 1200 | 1200 | 1200 | 1200 | 1200 |
| resin utilization | BV/hr where BV=total resin vol | 0.135 | 0.135 | 0.135 | 0.200 | 0.200 | 0.200 |
| step time | min | 8.75 | 8.75 | 8.75 | 8.92 | 8.92 | 8.50 |
| HFCS42 feed | mL/min | 2.7 | 2.7 | 2.7 | 4.0 | 4.0 | 4.0 |
| water | mL/min | 19.0 | 19.0 | 15.0 | 16.0 | 16.0 | 17.0 |
| HFCS42 to elution | mL/min | 0.0 | 0.0 | 0.0 | 0.0 | 0.0 | 0.0 |
| enrich | mL/min | 11.1 | 11.1 | 11.1 | 9.5 | 10.0 | 10.1 |
| reload | mL/min | 0.0 | 0.0 | 0.0 | 0.0 | 0.0 | 0.0 |
| water/feed | v/v | 7.0 | 7.0 | 5.6 | 4.0 | 4.0 | 4.3 |
| water/feed assuming volume is conserved through raffinate recycling* | v/v | | | | | | |
| extract fructose yield | % of fructose from feed and desorb | 95.1 | 95.2 | 94.4 | 97.0 | 94.9 | 96.6 |
| extract fructose purity | % of total sugars excluding DP4+** | 95.0 | 96.6 | 96.5 | 68.2 | 74.7 | 72.2 |
| extract total sugars | %w/w excluding DP4+ | 11.7 | 10.4 | 21.5 | 25.9 | 21.3 | 22.4 |
| raffinate fructose yield | % of fructose from feed and desorb | 4.4 | 4.0 | 4.6 | 2.5 | 1.9 | 2.6 |
| raffinate fructose purity | % of total sugars excluding DP4+ | 3.7 | 3.2 | 3.7 | 2.8 | 1.9 | 2.8 |
| raffinate total sugars | %w/w excluding DP4+ | 7.9 | 7.6 | 7.8 | 8.2 | 7.5 | 7.8 |

* predicted water req = water flow + HFCS42 flow into el - raffinate flow

** all reported experiments resulted in approximately the same total sugars in feed and extract, a requirement for full recycling of raffinate through a GI column into the eluent

Figure 5

| date | | 2/9/2013 | 2/11/2013 | 2/13/2013 | 2/14/2013 | 2/15/2013 | 3/1/2013 |
|---|---|---|---|---|---|---|---|
| resin | UBK555-Ca | | | | | | |
| geometry | elution-enrich-feed-reload | 1-3-3-1 | 1-3-3-1 | 1-3-3-1 | 1-3-3-1 | 1-3-3-1 | 1-3-3-1 |
| total resin volume | mL | 1200 | 1200 | 1200 | 1200 | 1200 | 1200 |
| resin utilization | BV/hr where BV=total resin vol | 0.200 | 0.200 | 0.200 | 0.200 | 0.200 | 0.200 |
| step time | min | 8.92 | 8.92 | 8.92 | 8.92 | 8.92 | 8.75 |
| HFCS42 feed | mL/min | 4.0 | 4.0 | 4.0 | 4.0 | 4.0 | 4.0 |
| water | mL/min | 9.0 | 7.0 | 9.0 | 7.0 | 6.0 | 15.0 |
| HFCS42 to elution | mL/min | 0.0 | 0.0 | 0.0 | 0.0 | 0.0 | 0.0 |
| enrich | mL/min | 10.0 | 10.0 | 10.0 | 10.0 | 10.0 | 9.8 |
| reload | mL/min | 7.0 | 9.0 | 7.0 | 9.0 | 10.0 | 0.0 |
| water/feed | w/v | 2.3 | 1.8 | 2.3 | 1.8 | 1.5 | 3.8 |
| water/feed assuming volume is conserved through raffinate recycling** | w/v | | | | | | |
| extract fructose yield | % of fructose from feed and desorb | 93.9 | 93.1 | 93.6 | 92.4 | 92.2 | 93.6 |
| extract fructose purity | % of total sugars excluding DP4+ | 64.3 | 59.8 | 77.4 | 76.9 | 72.4 | 72.5 |
| extract total sugars | %w/w excluding DP4+ | 27.4 | 29.4 | 22.4 | 24.7 | 26.1 | 28.7 |
| raffinate fructose yield | % of fructose from feed and desorb | 5.5 | 4.8 | 8.0 | 7.2 | 7.1 | 5.8 |
| raffinate fructose purity | % of total sugars excluding DP4+ | 6.7 | 6.8 | 7.2 | 7.4 | 7.8 | 6.0 |
| raffinate total sugars | %w/w excluding DP4+ | 14.1 | 16.8 | 18.7 | 25.1 | 28.7 | 8.7 |

*predicted water req = water flow + HFCS42 flow into el – raffinate flow

**all reported experiments resulted in approximately the same total sugars in feed and extract, a requirement for full recycling of raffinate through a GI column into the eluent

Figure 6

| date | | 3/13/2013 | 3/14/2013 | 3/15/2013 | 3/20/2013 | 3/26/2013 | 3/27/2013 | 3/28/2013 |
|---|---|---|---|---|---|---|---|---|
| resin | UBK555-Ca | | | | | | | |
| geometry | elution-enrich-feed-reload | 2-3-3-0 | 2-3-3-0 | 2-3-3-0 | 2-3-3-0 | 2-3-3-0 | 2-3-3-0 | 2-3-3-0 |
| total resin volume | mL | 1200 | 1200 | 1200 | 1200 | 1200 | 1200 | 1200 |
| resin utilization | BV/hr where BV=total resin vol | 0.135 | 0.135 | 0.135 | 0.135 | 0.135 | 0.135 | 0.135 |
| step time | min | 8.75 | 8.75 | 8.75 | 8.75 | 8.75 | 8.75 | 8.75 |
| HFCS42 feed | mL/min | 2.7 | 2.7 | 2.7 | 2.7 | 2.7 | 2.7 | 2.7 |
| water | mL/min | 15.2 | 15.0 | 14.0 | 10.5 | 8.1 | 8.1 | 8.1 |
| HFCS42 to elution | mL/min | 3.8 | 4.0 | 4.0 | 5.9 | 6.9 | 6.9 | 6.9 |
| enrich | mL/min | 11.1 | 11.1 | 11.1 | 11.1 | 11.1 | 11.1 | 11.1 |
| reload | mL/min | 0.0 | 0.0 | 0.0 | 0.0 | 0.0 | 0.0 | 0.0 |
| water/feed | w/v | 5.6 | 5.6 | 5.2 | 3.9 | 3.0 | 3.0 | 3.0 |
| water/feed assuming volume is conserved through raffinate recycling* | w/v | 1.9 | 1.9 | 1.6 | 0.8 | 0.4 | 0.4 | 0.4 |
| extract fructose yield | % of fructose from feed and desorb | 58.3 | 58.6 | 56.1 | 48.3 | 37.1 | 37.0 | 37.0 |
| extract fructose purity | % of total sugars excluding DP4+ | 63.9 | 63.8 | 63.6 | 62.0 | 59.5 | 59.4 | 59.8 |
| extract total sugars | %w/w excluding DP4+ | 22.4 | 23.8 | 25.7 | 35.3 | 42.9 | 42.9 | 43.3 |
| raffinate fructose yield | % of fructose from feed and desorb | 40.8 | 41.3 | 43.5 | 54.4 | 62.6 | 62.6 | 62.5 |
| raffinate fructose purity | % of total sugars excluding DP4+ | 30.2 | 31.0 | 31.6 | 36.9 | 39.5 | 39.6 | 39.6 |
| raffinate total sugars | %w/w excluding DP4+ | 18.8 | 19.3 | 20.1 | 26.3 | 32.3 | 32.3 | 32.3 |

* predicted water req = water flow + HFCS42 flow into el - raffinate flow

** all reported experiments resulted in approximately the same total sugars in feed and extract, a requirement for full recycling of raffinate through a GI column into the eluent

Figure 7

| state | | 90% of parent resin utilization | | | | 92.5% of parent resin utilization | | | |
|---|---|---|---|---|---|---|---|---|---|
| | | 8/22/2013 | 8/23/2013 | 8/25/2013 | 8/26/2013 | 8/27/2013 | 8/28/2013 | 8/31/2013 | 9/1/2013 |
| resin | UOP 5.5 Ca | | | | | | | | |
| resin volume | mL | 2672 | 2672 | 2672 | 2672 | 2672 | 2672 | 2672 | 2672 |
| resin utilization | BV/hr where BV=total resin vol | 0.088 | 0.088 | 0.088 | 0.119 | 0.119 | 0.119 | 0.119 | 0.119 |
| | | | | | | | | | |
| feed sugars setting | mln | 8.00 | 8.30 | 8.90 | 5.20 | 5.20 | 5.20 | 5.40 | 5.40 |
| desorb pump setting | mln | 17.00 | 17.90 | 17.00 | 11.00 | 11.00 | 11.00 | 12.60 | 12.60 |
| | | | | | | | | | |
| feed pump setting | mL/min | 12.2 | 12.2 | 13.2 | 16.3 | 16.5 | 16.5 | 17.0 | 17.0 |
| desorb pump setting | mL/min | 17.0 | 17.0 | 17.5 | 26.2 | 26.2 | 30.0 | 24.5 | 24.5 |
| extract pump setting | mL/min | 10.6 | 10.6 | 11.1 | 17.9 | 17.9 | 20.0 | 18.0 | 18.7 |
| raffinate setting | mL/min | 18.6 | 18.6 | 18.6 | 24.8 | 24.8 | 26.3 | 24.1 | 24.4 |
| smash setting | mL/min | 6.4 | 6.4 | 6.4 | 8.3 | 8.3 | 10.0 | 6.5 | 6.6 |
| recycle pump setting | mL/min | 17.9 | 17.7 | 17.7 | 28.0 | 27.7 | 27.7 | 25.0 | 24.8 |
| | | | | | | | | | |
| feed total sugars avg addition rate | g/min | 2.90 | 2.91 | 2.96 | 3.95 | 3.97 | 4.09 | 4.06 | 4.06 |
| desorb total sugars avg addition rate | g/min | 0.00 | 0.00 | 0.00 | 0.00 | 0.00 | 0.00 | 0.00 | 0.00 |
| extract total sugars avg elution rate | g/min | 1.22 | 1.26 | 1.30 | 1.75 | 1.80 | 1.68 | 1.83 | 1.81 |
| raffinate total sugars avg elution rate | g/min | 1.66 | 1.62 | 1.63 | 2.19 | 2.19 | 2.21 | 2.21 | 2.32 |
| | | | | | | | | | |
| extract fructose yield | % of feed total desorb to fructose | 92.8 | 88.3 | 88.5 | 93.3 | 96.8 | 88.9 | 82.8 | 92.3 |
| | | | | | | | | | |
| feed fructose | %w/wt | 25.5 | 25.5 | 26.0 | 25.2 | 25.8 | 26.2 | 26.7 | 26.7 |
| feed total sugars | %w/wt | 58.4 | 58.6 | 59.4 | 59.1 | 59.2 | 59.7 | 60.8 | 60.7 |
| feed fructose purity | % of total sugars | 43.6 | 43.5 | 43.5 | 43.3 | 43.5 | 43.9 | 44.0 | 44.0 |
| | | | | | | | | | |
| desorb fructose | %w/wt | 0.0 | 0.0 | 0.0 | 0.0 | 0.0 | 0.0 | 0.0 | 0.0 |
| desorb total sugars | %w/wt | 0.0 | 0.0 | 0.0 | 0.0 | 0.0 | 0.0 | 0.0 | 0.0 |
| desorb fructose purity | % of total sugars | | | | | | | | |
| | | | | | | | | | |
| extract fructose | %w/wt | 30.4 | 30.8 | 30.3 | 25.3 | 25.6 | 22.7 | 27.4 | 26.4 |
| extract total sugars | %w/wt | 31.7 | 32.5 | 32.2 | 27.6 | 28.2 | 24.0 | 30.1 | 29.0 |
| extract fructose purity | % of total sugars | 95.9 | 96.7 | 93.2 | 91.8 | 88.4 | 88.7 | 90.8 | 91.8 |
| | | | | | | | | | |
| raffinate fructose | %w/wt | 1.3 | 1.0 | 0.9 | 1.1 | 0.8 | 0.7 | 1.4 | 1.4 |
| raffinate total sugars | %w/wt | 25.1 | 24.8 | 24.6 | 24.5 | 24.3 | 24.4 | 27.3 | 27.0 |
| raffinate fructose purity | % of total sugars | 5.0 | 3.9 | 3.7 | 4.4 | 3.5 | 2.9 | 5.2 | 5.2 |

Figure 8

| date | | 9/19/2013 | 9/20/2013 | 9/25/2013 | 9/26/2013 | 9/26/2013 |
|---|---|---|---|---|---|---|
| resin | | UBK555-Ca | | | | |
| resin volume | mL | 2672 | 2672 | 2672 | 2672 | 2672 |
| resin utilization | BV/hr where BV=total resin vol | 0.119 | 0.119 | 0.119 | 0.119 | 0.119 |
| | | | | | | |
| feed substep time | min | 5.20 | 5.20 | 5.20 | 5.20 | 5.20 |
| recycle substep time | min | 11.05 | 11.05 | 11.05 | 11.05 | 11.05 |
| | | | | | | |
| feed pump setting | mL/min | 16.5 | 16.5 | 16.5 | 16.5 | 16.5 |
| desorb pump setting | mL/min | 26.2 | 26.2 | 26.2 | 26.2 | 26.2 |
| extract pump setting | mL/min | 17.9 | 17.9 | 18.4 | 18.4 | 18.9 |
| raffinate setting | mL/min | 24.8 | 24.8 | 24.3 | 24.3 | 23.8 |
| enrich setting | mL/min | 8.3 | 8.3 | 7.8 | 7.8 | 7.3 |
| recycle pump setting | mL/min | 27.7 | 27.7 | 27.7 | 27.7 | 27.7 |
| | | | | | | |
| feed total sugars avg addition rate | g/min | 3.79 | 3.77 | 4.04 | 4.04 | 4.11 |
| desorb total sugars avg addition rate | g/min | 2.94 | 3.42 | 2.82 | 2.82 | 2.78 |
| extract total sugars avg elution rate | g/min | 3.31 | 3.54 | 3.50 | 3.50 | 3.67 |
| raffinate total sugars avg elution rate | g/min | 3.37 | 3.57 | 3.37 | 3.37 | 3.25 |
| | | | | | | |
| extract fructose yield | % of feed and desorb fructose | 63.8 | 60.1 | 66.4 | 66.4 | 68.8 |
| | | | | | | |
| feed fructose | %w/w | 27.8 | 28.2 | 27.6 | 27.6 | 28.0 |
| feed total sugars | %w/w | 60.0 | 61.9 | 60.5 | 60.5 | 61.5 |
| feed fructose purity | % of total sugars | 45.6 | 45.6 | 45.6 | 45.6 | 45.6 |
| | | | | | | |
| desorb fructose | %w/w | 13.8 | 16.2 | 13.7 | 13.7 | 13.7 |
| desorb total sugars | %w/w | 30.8 | 35.5 | 30.2 | 30.2 | 30.2 |
| desorb fructose purity | % of total sugars | 44.9 | 45.6 | 45.5 | 45.5 | 45.5 |
| | | | | | | |
| extract fructose | %w/w | 28.2 | 28.3 | 29.2 | 29.2 | 29.5 |
| extract total sugars | %w/w | 48.0 | 50.9 | 49.2 | 49.2 | 50.3 |
| extract fructose purity | % of total sugars | 58.8 | 55.7 | 59.3 | 59.3 | 58.7 |
| | | | | | | |
| raffinate fructose | %w/w | 11.7 | 14.4 | 11.7 | 11.7 | 11.7 |
| raffinate total sugars | %w/w | 37.7 | 40.7 | 38.0 | 38.0 | 37.8 |
| raffinate fructose purity | % of total sugars | 31.1 | 35.4 | 30.9 | 30.9 | 30.8 |

~120% of plant resin utilization with HFCS42 addition to eluent

| Run # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Feed (16) (ml/min) | 8 | 8 | 8 | 8 | 8 | 8 | 8 | 8 | 8 | 8.7 | 8.7 | 8.7 | 8.7 | 8.7 | 8.7 | 8.7 |
| Water only (38) (ml/min) | 11.5 | 12 | 14 | 14.5 | 14.5 | 14.5 | 14.5 | 14.5 | 14.5 | 12 | 12 | 12 | 12 | 13 | 13 | 13 |
| Feed Eluent pulse (26) (ml/min) | 0 | 12 | 12 | 12 | 12 | 11.7 | 11.7 | 11.7 | 11.7 | 0 | 11.7 | 11.7 | 11.7 | 11.7 | 11.7 | 11.7 |
| Water : Feed | 1.44 | 0.92 | 1.07 | 1.11 | 1.11 | 1.11 | 1.11 | 1.11 | 1.11 | 1.38 | 0.84 | 0.84 | 0.84 | 0.91 | 0.91 | 0.91 |
| Feed Eluent Time (min) | 0 | 3 | 3 | 3 | 3 | 3 | 3 | 3 | 3 | 0 | 3 | 3 | 3 | 3 | 3 | 3 |
| Water only Time (min) | 7.7 | 4.7 | 4.7 | 4.7 | 4.7 | 4.7 | 4.7 | 4.7 | 4.7 | 7.7 | 4.7 | 4.7 | 4.7 | 4.7 | 4.7 | 4.7 |
| Production (% of Theoretical) | 110% | 70% | 84% | 90% | 83% | 84% | 93% | 97% | 97% | 133% | 79% | 56% | 89% | 92% | 93% | 96% |
| Extract : Feed Sugars | 44% | 90% | 90% | 91% | 100% | 99% | 103% | 93% | 102% | 47% | 81% | 66% | 78% | 83% | 77% | 80% |
| Water Savings (Per 55 production) | 4.80% | 4.90% | 7.70% | 11.00% | 3.10% | 4.10% | 13.50% | 17.00% | 17.00% | 18.40% | 15.80% | -17.70% | 25.40% | 21.50% | 23.00% | 25.20% |
| Extract Fx Purity (30) | 86.1 | 56 | 59.2 | 59.7 | 57.1 | 57.4 | 58 | 61.1 | 60.4 | 59.4 | 57.4 | 56.6 | 60.3 | 59.7 | 61.4 | 61.3 | ns
METHOD FOR ADJUSTING THE COMPOSITION OF CHROMATOGRAPHY PRODUCTS

CROSS-REFERENCE TO RELATED APPLICATIONS

The present application is a national stage entry of International Application No. PCT/US2015/055224, filed Oct. 13, 2015, which itself claims the benefit of U.S. Provisional Patent Application No. 62/063,476, filed Oct. 14, 2014, each of the contents of the entirety of which are incorporated by this reference.

FIELD OF THE INVENTION

The invention is related generally to the use of simulated moving bed chromatography to separate and enrich sugar or other components in a mixture with limited dilution, and more particularly to methods for preparing an enriched high fructose corn syrup (HFCS) containing a higher concentration of fructose than obtained from the action of glucose isomerase at equilibrium without need to blend the lower % equilibrium syrup with a higher % percent fructose enriched syrup.

DESCRIPTION OF RELATED ART

High fructose corn syrup (HFCS) is a well-known sweetener obtained from corn starch that has certain defined proportions of fructose and glucose. HFCS is conventionally obtained by (a) liquefaction and hydrolysis of corn starch with heat, alpha amylase and glucoamylase to form an aqueous glucose syrup known as corn syrup, having approximately 95% glucose, and (b) isomerization of a portion of the glucose in the corn syrup using a column-bound glucose isomerase, at 60° C., until the material approaches the equilibrium point of the isomerase, which generally produces a syrup mixture that is about 42%-44% fructose and about 56%-58% glucose (referred to herein as 42% fructose syrup or more simply 42 syrup).

Many food and beverage manufacturers desire a HFCS product where the fructose proportion is greater than the glucose proportion to more closely mimic the taste profile of sucrose. The most typically desired HFCS product is a 55% fructose syrup, however, some consumers desire HFCS products containing as much as 90% fructose. To achieve these higher fructose proportions the 42% fructose syrup obtained from the isomerase column is subjected to chromatographic separation over a divalent cation resin that preferentially retards and therefore enriches the fructose relative to the glucose in an enrichment zone of the column. Typically the cation is calcium on a sulfonic acid resin. The chromatographic resin is eluted with water as the mobile phase to obtain a HFCS product that is about 90% fructose (90% fructose syrup). This 90% fructose product is then blended with the 42% fructose syrup from the isomerase column to achieve HFCS products with fructose proportions greater than 50%, and less than 90%, most preferably about 55%.

Typically the chromatographic enrichment process uses a simulated moving bed (SMB) chromatography apparatus. SMB chromatography operates by dividing a column bed into multiple discrete inter-connected column segments, introducing the input feed and eluent feed in a common flow direction over the linked column segments while essentially moving the column segments in a direction opposite the flow direction of the input and eluent streams. In some designs this is accomplished directly by actually rotating the column segments in a circular carousel in a direction opposite to the flow of the input and eluent streams. In other designs, the column segments are stationary but the ports for input and output of the column segments are rotated in the same direction as the flow of input and eluent streams. In either design, the rotation is herein referred to as a step or a step movement. In either case the effect is the same, the material that preferentially retards with the stationary phase in the column segments (e.g., fructose in HFCS production) is preferentially carried with the column segments opposite in direction to the flow of material that preferentially flows with the moving phase eluent (e.g., glucose with water in HFCS production) across the whole length of the interconnected column segments. The material that preferentially retards with the stationary phase is collected as an extract product and the material that preferentially flows with the moving phase eluent is collected in a raffinate stream.

Figure 1:
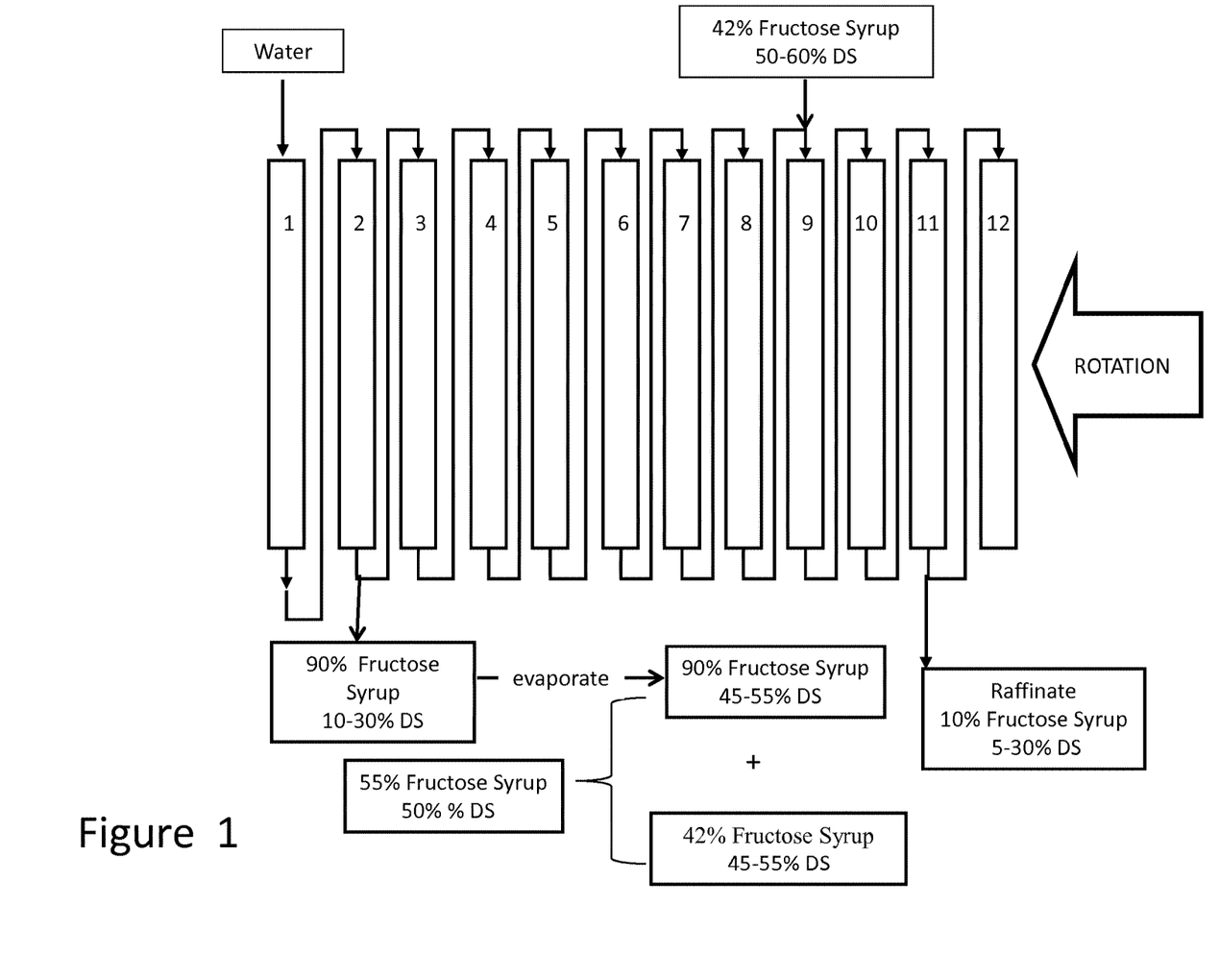
FIG. 1 is schematic view of a conventional SMB apparatus employed in methods of the prior art to enrich HFCS from a 42% fructose syrup to a 55% fructose syrup. The line arrows show the direction of flow of the fluid, the large arrow depicts the counter directional movement of the column segments in the SMB apparatus. The boxes show the typical ranges of dissolved solids in the input and output streams.

When input and eluent stream flow rates are properly coordinated with column segment movements, the result is a continuous standing wave of zones of feedstock input, zones of enrichment, zones of elution, and zones of recover (optional). In the case of HFCS production, syrup containing about 90% fructose/10% glucose is collected as the extract product and a syrup containing about 10% fructose/90% glucose is collected in the raffinate stream. A conventional HFCS production process using an SMB apparatus with a 42% fructose/58% glucose feed, a water eluent feed, a fructose-enriched extract product and a glucose-enriched raffinate stream is depicted in FIG. 1.

Two drawbacks of the conventional method of making HFCS are that first, it requires an additional input of water as the eluent, which increases cost. Second, the chromatographic enrichment of fructose using water as the eluent results in dilution of the total sugar concentration in the extract product and the raffinate stream. Typically the input stream of 42-44% fructose has a dissolved solids content of 45% to 60%, the 90% fructose syrup in the extract product has a dissolved solids content of 10% to 30%, and the glucose-enriched raffinate stream has a dissolved solids content of about 5-30%. In order to produce a product having a commercially desirable dissolved solids concentration of at least 50% DS and typically about 70% DS, the 90% fructose extract product is typically evaporated to a desired concentration that is at least the same as the 42% fructose input feed before blending to make a product such as 55% HFC as illustrated in FIG. 1. The need for evaporation increases cost of operation.

BRIEF SUMMARY OF THE INVENTION

One exemplary embodiment of the present invention is directed to a method of adjusting the composition of a chromatography product to achieve a target proportion of a desired component by contacting an input zone of a simulated moving bed ("SMB") chromatography apparatus comprising a cation resin with an input feed comprising input feed proportions of the desired component and a second component and having an input feed dissolved solids content, and contacting an elution zone of the SMB apparatus with an eluent feed comprising eluent feed proportions of the desired component and the second component and having an eluent feed dissolved solids content.

In certain exemplary embodiments, the SMB apparatus is operated to blend the desired component from the input feed, delivered through an enrichment zone of the SMB apparatus, with the desired component from the eluent feed, delivered though the elution zone, to form an extract product comprising the target proportion of the desired component and an extract dissolved solids content, wherein the target proportion of the desired component is greater than the input feed proportion of the desired component, and wherein the extract dissolved solids content is at least 50% of the input feed dissolved solids content. In more desirable embodiments the dissolved solids content of the extract is at least 60% of the input feed dissolved content, and in the most desired embodiments the dissolved solids content of the extract is at least 80% of the input feed dissolved content. The extract product having the target proportion of the desired component is collected from the SMB apparatus.

In certain exemplary embodiments of the invention, the eluent feed proportion of the desired component is selected to blend with the desired component from the input feed delivered through the enrichment zone to result in the target proportion of the desired component in the extract product.

In some exemplary embodiments, the eluent feed is the same as the input feed or the eluent feed is diluted no more than 0.2 volumes of water prior to contacting the elution zone.

In certain embodiments, the eluent feed is continuously combined with water to contact the elution zone with a diluted eluent feed, wherein a volume ratio of eluent feed to water is 1:2.

In certain exemplary embodiments, the eluent feed is contacting the elution zone for a period of time, followed by a second period of time where water is contacting the elution zone without the eluent feed, wherein the first period of time and the second period of time are selected so that a volume ratio of eluent feed to water is 1:2 prior to a step movement in the SMB apparatus.

In certain exemplary embodiments, the method of the present invention further comprises collecting from the SMB apparatus a raffinate stream having raffinate proportions of the desired component and the second component, wherein the raffinate proportion of the second component is higher than the input feed proportion of the second component.

In some exemplary embodiments, the method of the present invention can be used wherein the desired component is fructose and the second component is glucose.

In certain embodiments, the raffinate stream comprises glucose and is added to an input stream comprising glucose to form a combined glucose-enriched stream. A glucose isomerase chromatography column comprising glucose isomerase is contacted with the raffinate stream and/or combined glucose-enriched stream for a time sufficient to enrich a fructose proportion in the column. The fructose-enriched mixture is eluted from the glucose isomerase column. The eluted fructose-enriched mixture can be used in the input feed that contacts the input zone of the SMB apparatus. The glucose isomerase column can be contacted for less than a time required to bring the proportions of fructose and glucose to an equilibrium point for the glucose isomerase, whereby the eluted fructose-enriched mixture has a lower fructose proportion than would be obtained by contacting the glucose isomerase column for the time required to bring the proportions of fructose and glucose to the equilibrium point for the glucose isomerase.

In some embodiments, no water is added to the SMB apparatus that would dilute the extract dissolved solids content in comparison to the input feed dissolved solids content. The input feed dissolved solids content and the extract dissolved solids content can each be at least 50% wt/vol.

In any of the embodiments described herein, the desired component may be fructose and the second component may be glucose. In one exemplary embodiment, the input feed proportion of fructose is 42-44%, and the target proportion of fructose in the extract product is 55%-60%.

In certain exemplary embodiments, the method is used to adjust the proportion of fructose in a high fructose corn syrup product to achieve a target proportion of fructose. A simulated moving bed ("SMB") chromatography apparatus containing a cation resin that facilitates enrichment of fructose over glucose in a fructose enrichment zone of the SMB apparatus is contacted with an input feed and an eluent feed. Each of the input feed and the eluent feed comprises mixtures of fructose and glucose and has a dissolved solids content. The SMB apparatus is operated to produce in the fructose enrichment zone the high fructose corn syrup product having the target proportion of fructose and a product dissolved solids content. The high fructose corn syrup product having the target proportion of fructose is collected from the fructose enrichment zone of the SMB apparatus.

In some exemplary embodiments, the high fructose corn syrup product has a dissolved solids content at least 50%, at least 60% or at least 80% of the dissolved solids content of the input feed.

Some exemplary embodiments comprise a method of optimizing the operational costs of producing a high fructose corn syrup product having a target proportion of fructose. The method includes operating a simulated moving bed ("SMB") apparatus to achieve the target proportion of fructose as described herein, collecting a glucose-enriched raffinate stream from the SMB apparatus wherein the glucose proportion in the raffinate stream is higher than the glucose proportion in the input feed as described herein, using the glucose-enriched raffinate stream as an input stream for a glucose isomerase column as described herein, operating the glucose isomerase column to convert glucose in the input stream to fructose to produce a fructose-enriched mixture having determined proportions of fructose and glucose, wherein the input feed of the contacting comprises the fructose-enriched mixture, and using a linear program model to minimize the total costs incident to:

(a) replacing the glucose isomerase column as affected by the determined proportions of fructose to glucose in the fructose-enriched mixture;

(b) the frequency of replacing the cation resin in the SMB apparatus;

(c) removal of water from an output stream of either of both of the SMB apparatus and glucose isomerase column; and (d) maximizing production of the target high fructose corn syrup product per unit of cost.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 8 is a table disclosing the results of an experiment from Example 2 using water mixed with 42% syrup.

DETAILED DESCRIPTION OF PREFERRED EMBODIMENTS

The present invention is directed to a method of adjusting the composition of a chromatography product to achieve a target enrichment of a component in a product mixture using simulated moving bed ("SMB") chromatography, wherein the eluent comprises the desired component in the same or roughly the same ratio as the mixture that is used as an input stream for the SMB chromatography system and wherein there is minimum dilution of the target product mixture. In a preferred operation, one or both of the input stream or the eluent is made by recycling the raffinate stream from the SMB chromatography system, which the raffinate stream contains the same components in a different ratio than desired in the target product. The method is particularly well suited to a process for adjusting the fructose content in a high fructose corn syrup product and in the most preferred embodiment, a glucose isomerase column is used to modify the raffinate stream for re-introduction into the SMB apparatus as the eluent and/or input stream. Exemplary processes allow for the production of 50%-65% HFCS product using only a 42% fructose syrup as input eluent, and most exemplary by production of 55% fructose syrup from a 42% syrup without substantial dilution relative to the 42% syrup used as the starting material. The process can be adapted to adjust the proportion of any components in a mixture that can be enriched by SMB chromatography where the target output stream has a purity for one component that is greater than an input stream containing the component but less than the highest purity that can be achieved by the SMB chromatography process where it is desired to minimize dilution of the final output product.

In the method of the present invention, by using an eluent containing the desired component to replace all or some of the water in the eluent the cost of production is reduced as a result of lower water usage and reduced need for energy to evaporate. In addition, the dissolved solids content of the extract product is increased, which reduces the need to evaporate the extract product to increase the concentration of the desired component. In the embodiments wherein the eluent feed is derived from recycling of the raffinate stream, the process further allows for the recovery in the final product of much, if not all, of the fructose from the input feed by recycling the raffinate through a glucose isomerase column back to the SMB apparatus.

As used herein, unless expressly defined otherwise, a reference to a "X % fructose syrup" refers to an aqueous syrup containing fructose and glucose with fructose representing X % of the sugar and glucose the remaining percent (100–X) %. All references of amounts of glucose, fructose, or dissolved solids herein are inclusive of residual disaccharides and oligosaccharides which are typically present in insignificant quantities in sugar syrups made by liquefaction of starch which are ignored herein. Thus 42% fructose syrup means the proportion of sugar that is fructose is 42% fructose and the proportion that is glucose is 58% ignoring the fact that the precise percentage of either may be slightly less due to the presence of some residual sugars. "X % concentration," refers to the wt/wt percent of the referenced dissolved species per total syrup weight unless with express reference to "dissolved solids content" e.g., X % DS, which is the total wt/wt percent of fructose and glucose combined per weight of syrup solution. Thus for example, a 55% fructose syrup at a dissolved solids content of 20% means there are 20 g of total dissolved sugars per 100 g of syrup solution weight, and out of the 20 grams of sugar 11 g is fructose and 9 g is glucose with the concentration of fructose in the syrup being 11% g/g and the concentration of glucose being 9% g/g.

Figure 2:
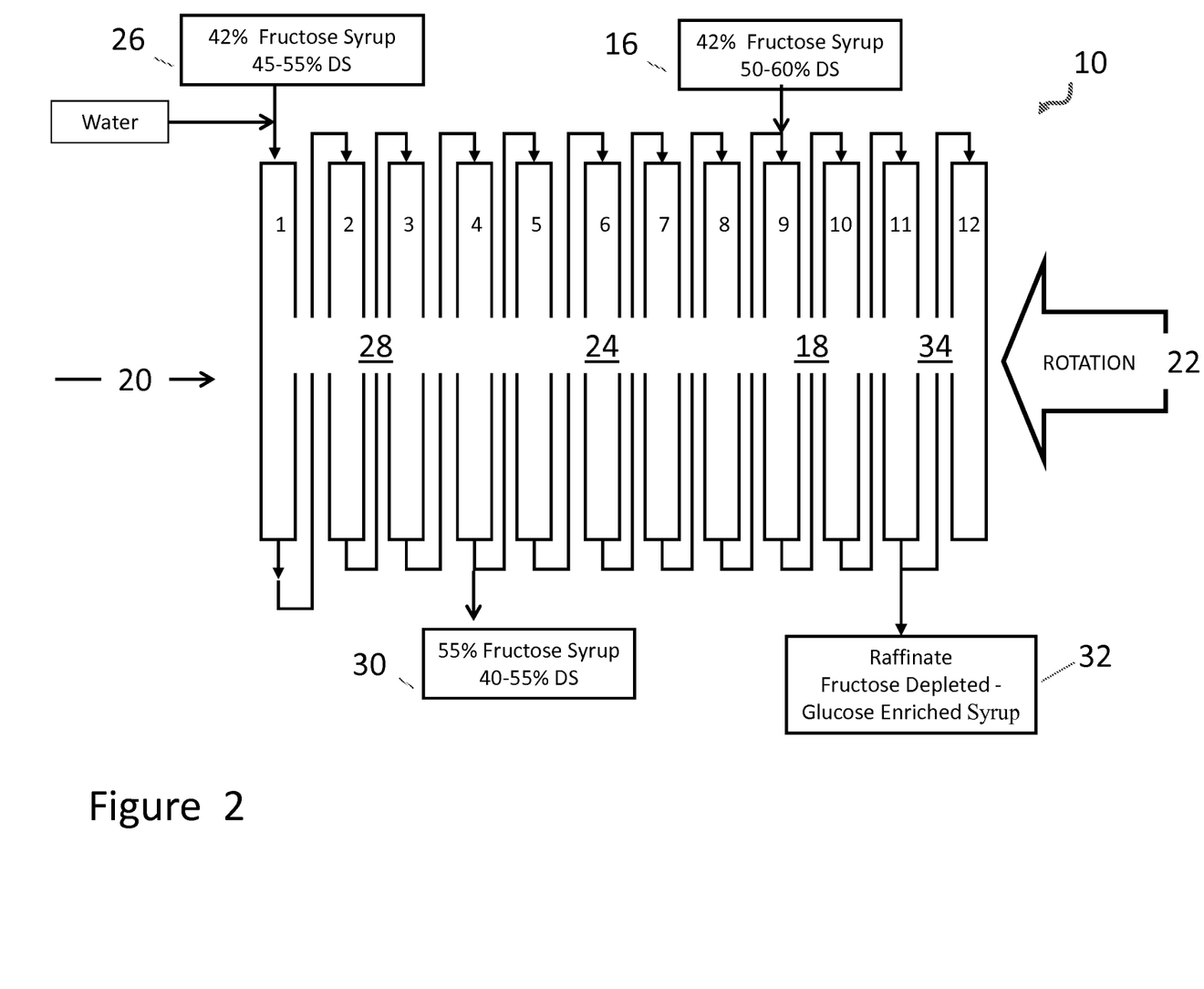
FIG. 2 is a schematic view of a SMB apparatus configured for use in the method of the present invention to enrich a 42% fructose syrup to a 55% fructose syrup with minimum change in dissolved solids concentration.

An exemplary embodiment of the present invention using simulating moving bed (SMB) chromatographic apparatus 10 is illustrated in FIG. 2. SMB apparatus 10 includes a continuous stationary phase column bed separated into a plurality (1-12) of segmented columns on a carousel of SMB apparatus 10. The output from the bottom of each column segment n enters the top of the next column segment n+1 and all the columns are linked in this matter into a loop. In this exemplary embodiment, the stationary phase contained within the column segments is a cation exchange resin in the calcium form, which is typically used in the art for the chromatographic separation of sugars.

The input feed 16 is 42% fructose syrup typically having a dissolved solids content of 45-55% which is typically obtained directly from a glucose isomerase column that converts dextrose into 42% fructose syrup. As used herein 42% fructose syrup encompasses a syrup that is typically 42% to 44% fructose depending on how the glucose isomerase column is operated to initially convert dextrose (i.e., glucose made by liquefaction from starch) into glucose. The input feed 16 is input in to the SMB apparatus 10 at column segment 9, which along with segments 8 and 10 constitute input zone 18, and is passed from the bottom of column segment 9 to the top of the next adjacent bed column segment 10 in fluid flow direction 20. At the same time, the plurality of columns are rotated in the carousel in column movement direction 22 that is counter current to the fluid flow direction 20. The columns are linked in a circular carousel so a step movement will move column segment 1 to the position of column segment 12, while column segment 12 will be moved to the position of column segment 11, etc. The fructose in input feed 16 preferentially partitions with the stationary phase contained within the column segments relative to glucose, therefore, as the column segments are rotated in column movement direction 22 the fructose preferentially moves with the columns through enrichment zone 24. In contrast, the glucose in the input feed 16 preferentially partitions with the liquid phase relative to fructose and therefore flows in fluid flow direction 20 toward raffinate zone 34.

As stated above, in this exemplary embodiment for fructose syrup enrichment the input feed 16 is a mixture of fructose and glucose, more preferably a mixture being about a 42-44% fructose syrup and most typically a 42% fructose syrup. However, in more general embodiments the input feed may comprise any mixture of two or more ingredients where it is desired to enrich the proportion of one ingredient over the other by a continuous chromatographic separation. As used herein, continuous chromatographic separation is any separation technique where two or more species have different adsorption affinities for a solid stationary phase relative to a liquid moving phase, which are separated by flowing the liquid phase over the stationary phase so that one species moves more rapidly than the other but both are in continuous motion over the stationary phase. Non-limiting examples of other input feeds containing desired compounds for enrichment include racemic mixtures, other types of isomers and chemical species such as other sugars, polyols, esters and acetal mixtures. To conserve water it is desirable that the input feed 16 and eluent feed 26 each have as high a dissolved solids content as possible taking into consideration the economic cost of product concentration. In the exemplary embodiments illustrated herein, the input feed 16 and the eluent feed 26 are each a 42% fructose syrup having a dissolved solids content between about 45 and 60%, most typically about 50%, which is typically the output syrup obtained from the conversion of corn syrup dextrose to 42% fructose syrup by use of a glucose isomerase column, which may be concentrated by evaporation to about 60%.

Returning to FIG. 2, the desired enriched product, which as illustrated is 55% fructose syrup 30, is obtained by introducing eluent feed 26, which as illustrated is the same as the 42% fructose syrup that is used as the input stream 16. The eluent feed contacts SMB apparatus 10 at column segment 1 in elution zone 28 and also moves in fluid direction 20. Eluent feed 26 displaces a fructose-enriched extract mixture 30 which as illustrated is 55% fructose syrup from elution zone 28, which is collected from SMB apparatus 10 at column segment 4. Elution zone 28 extends from the position at which eluent feed 26 is introduced through the position at which extract mixture 30 is collected. The enrichment zone 24 extends from the position at which input feed 16 is introduced to the position at which extract mixture 30 is collected. Simultaneously with input of feed stream 16 with eluent stream 26 and with withdrawal of extract mixture 30, a raffinate stream 32 is withdrawn from raffinate zone 34. As exemplified in FIG. 2, the raffinate stream 32 is a glucose-enriched/fructose-depleted mixture relative to the input stream 16, typically containing between 15-20% fructose and 80-85% glucose.

As illustrated in FIG. 2, SMB apparatus 10 includes 12 column segments constituting one column bed. This is for illustrative purposes only. Depending on flow volume, dissolved solids content and relative affinity for the stationary phase and moving phase for the species to be separated, any configuration of a SMB apparatus 10 may be employed to separate and enrich species according to the present invention, provided only that there is sufficient segmentation in the SMB apparatus to be able to have a distinct input zone 18, enrichment zone 24, eluent zone 28 and raffinate collection zone 34. The invention has been practiced in a HFCS manufacturing operation with a SMB apparatus having as few as 4 column segments.

Preferably, at least one void volume (i.e., the volume of the entire column bed excluding the volume taken up by resin itself) of the combination of input stream 16 and elution stream 26 is flowed over the whole column bed before collecting raffinate stream 32. In some exemplary embodiments, the proportion of the second component in the raffinate stream is higher than the input feed proportion of the second component. In the exemplary embodiments wherein the desired component is fructose and the second component is glucose, an input feed containing 56-58% glucose can produce a raffinate stream comprising greater than 56-58% glucose, most typically about 80-85% glucose.

In some exemplary embodiments, the eluent feed is the same as the input feed, and in certain exemplary embodiments, the input feed and eluent feed are both about 42% fructose syrup obtained from a glucose isomerase column. In more general embodiments, the proportion of the desired component in the eluent feed can be greater or equal to the proportion of the desired component in the input feed. In certain embodiments, the eluent feed may comprise additional water, which will dilute the dissolved solids concentration of the eluent feed but which may be added in the eluent feed to move the undesired component (e.g., glucose) through the SMB apparatus toward the raffinate zone at a faster rate. In preferred embodiments, the eluent feed comprises the input feed combined with no more than 0.2 volumes of water. In one exemplary embodiment, the eluent feed comprises a 100:15 mixture of 42% fructose syrup: water. In certain other embodiments, water alone may be used as an initial starting eluent feed when the SMB process begins and the eluent feed is later switched to the higher fructose containing eluent to select different dissolved solids concentration or % fructose syrup in the desired extract.

Returning to FIG. 2, when the overall fluid flow between input feed 16 and eluent feed 26 is properly balanced with the removal of extract mixture 30 and raffinate stream 32, the effect is to establish continuous chromatographic separation and product enrichment that can be conducted indefinitely, subject only to the life of the column bed, producing extract product 30 having the target proportion of the desired component with a minimum use of extra water and consequential minimum dilution of the dissolved solids content of the product.

In exemplary embodiments, the target proportion of the desired component is greater than the input feed proportion of the desired component. In certain exemplary embodiments, wherein the input feed is 42-44% fructose, the target proportion of fructose in extract mixture 30 is between about 50 and 60% fructose, more preferably about 55-58% and most preferably 55% fructose.

In some exemplary embodiments, the dissolved solids content of the extract product is at least 50% of the input feed dissolved solids content. In more desirable embodiments the solids content of the extract is at least 60%, at least 80%, or can be at least 95% of the dissolved solids content of the input feed when minimal water is added to the eluent stream. In the exemplary embodiments the dissolved solids content in the input feed and the extract product are each at least 50% wt/wt. In some exemplary embodiments where the desired component is fructose, the dissolved solids content of input feed 16 is about 50-60% and the dissolved solids content of the extract product is 40-55%, typically at least about 50%. In certain exemplary embodiments, no water is added to the SMB apparatus that would dilute the dissolved solids content in the extract product in comparison to the dissolved solids content of the input feed.

Figure 3:
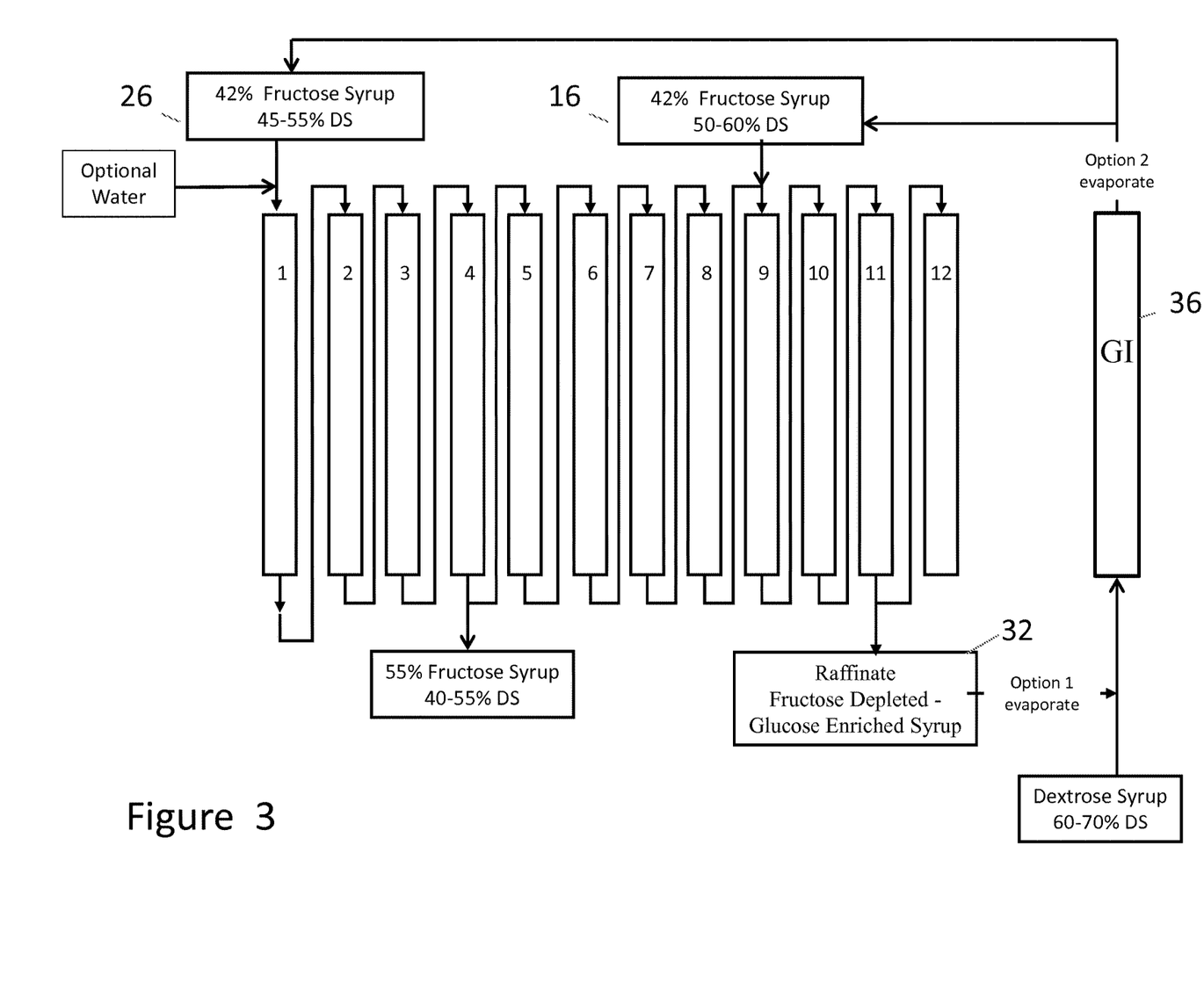
FIG. 3 is a schematic view of a SMB apparatus configured for use in the method of the present invention, in which the raffinate stream is diverted to a glucose isomerase column to convert the glucose to fructose forming further 42% fructose syrup for recycling onto the SMB apparatus.

In some embodiments, the raffinate stream 32 is recycled for use as the input 16 and/or eluent 26 streams. One example of such an embodiment is depicted in FIG. 3 where the raffinate stream 32 comprising enriched glucose and depleted fructose is diverted to a glucose isomerase column 36 to convert a portion of the glucose in the raffinate stream 32 into fructose reconstituting a fructose syrup sample similar to the original 42 fructose syrup with which it may be blended and used as the input 16 and/or eluent stream 26. To obtain the proper dissolved solids content, in one option the raffinate may be evaporated prior to introduction into the glucose isomerase column to the same dissolved solids typically used for the preparation of HFCS, which is in the range of 50-70%. In an alternative option, the output stream from the glucose isomerase column, which will be 42%-44% fructose, can be concentrated to the desired dissolved solids content of the eluent or input feed streams. In one embodiment the glucose isomerase column 36 may be one of the original glucose isomerase columns used to prepare the 42% fructose syrup from dextrose, in which case the raffinate stream 32 may optionally be blended with an input stream of dextrose. In such embodiments the higher content of fructose present in the raffinate stream relative to the dextrose stream means the glucose isomerase column can be operated at a faster flow rate and/or lower temperature to achieve a 42% fructose syrup. Also in such embodiments, evaporation of the raffinate stream 32 or output stream from the glucose isomerase column 36 may not be necessary if the dextrose syrup is at a high enough dissolved solids content so that the 42% syrup exiting the glucose isomerase column has the desired solids content for the eluent 26 or input 16 streams.

In alternative embodiments, the glucose isomerase column 36 configured with the SMB apparatus is optimized for operation solely with the raffinate stream 32 exiting the SMB apparatus, which means the glucose isomerase column. In addition, in embodiments where the eluent stream 26 contains added water, which will reduce the dissolved solids content but facilitate elution, the raffinate stream 32 typically has lower total dissolved solids content than input stream 16 so the flow rate of the glucose isomerase column can be higher than normally used to produce a 42% fructose syrup from dextrose.

Figure 9:
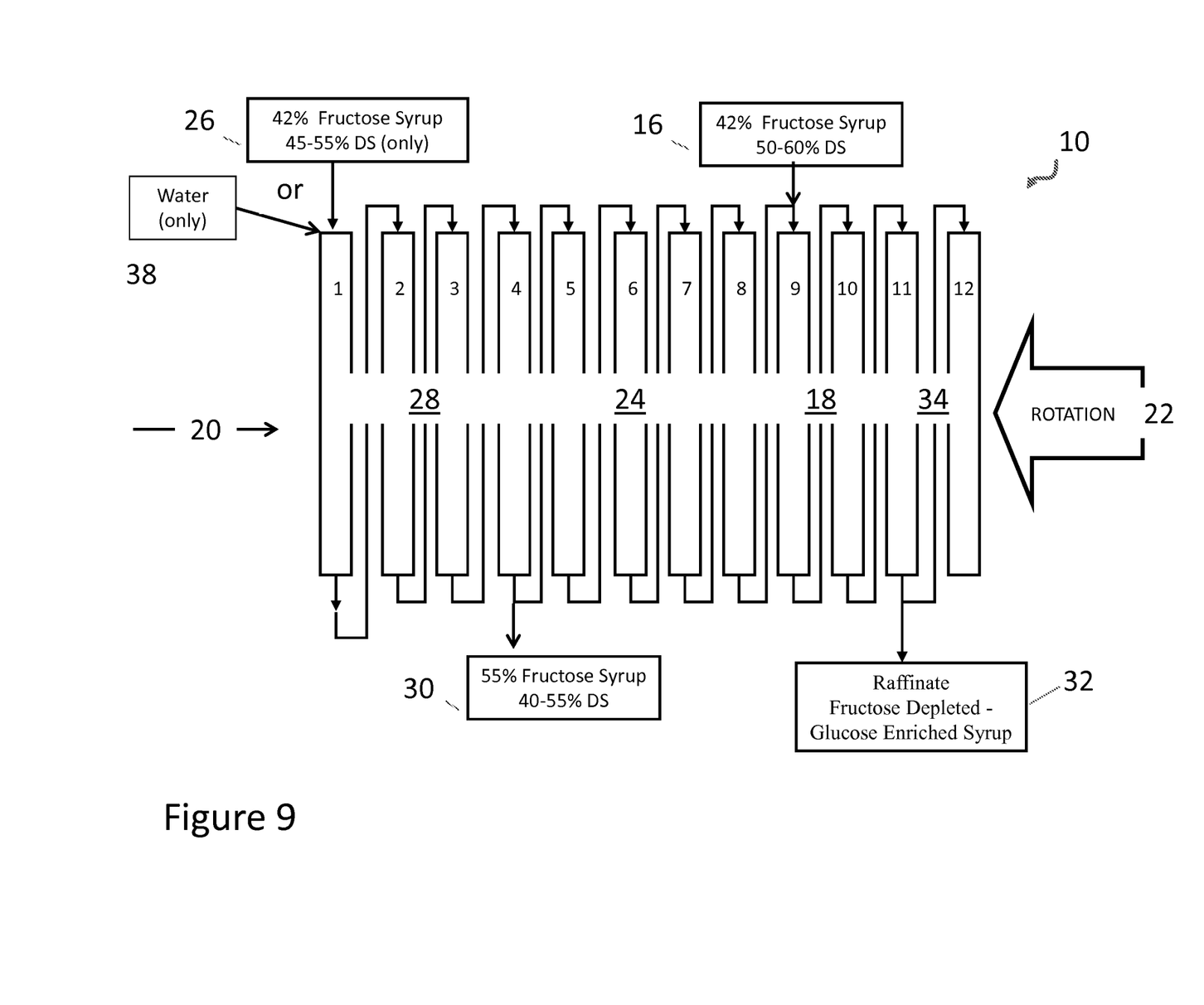
FIG. 9 is a schematic view of a SMB apparatus configured for use in the method of the present invention to enrich a 42% fructose syrup to a 55% fructose syrup with minimum change in dissolved solids concentration with a feed-water pulse as described in Example 3.

In alternative embodiments, rather than blending water to the eluent stream 26 to achieve the desired solid content, the eluent stream 26 flow is done as a feed-water pulse method. Eluent volume is herein described as the total volume of liquid input into the eluent stream. The eluent feed 26 enters into column 1 until 33% of the total eluent volume is achieved. The eluent feed 26 is then completely stopped and water only 38 enters column 1 for the duration of the step or until ~66% of the total eluent volume is achieved). This achieves a volume ratio of 1 part eluent feed to 2 parts water. Once the SMB apparatus rotates in the direction of 22, the step movement is completed and the water only 38 flow is stopped and the feed-water pulse is completed. The eluent feed 26 is turned back on and another feed-water pulse begins. The eluent feed 26 flows first, at the beginning of each step movement. Once the achieved volume of the eluent feed has been met, then the water only 38 flows until the end of the step movement. The water only 38 being fed after the eluent feed 26 helps to push the majority of the sugars into the elution zone 28 and hinders fructose from falling backwards as the SMB rotates into the Raffinate zone 34.

In certain embodiments, the eluent feed to water ratio is 1:4. In preferred embodiments, the eluent feed to water ratio is 1:3. In the most preferred embodiment, the eluent feed to water ratio is 1:2.

In certain embodiments it may be desirable to subject the raffinate stream 32 or the stream exiting the glucose isomerase column to an ion exchange column to remove cations that may have leached from the columns in the SMB apparatus.

The method of the present invention can be used to optimize the operational costs of producing a chromatography product having a target proportion of a desired component using a linear program model to minimize total costs incident to certain aspects of the method. In the exemplary embodiments wherein the method is used to produce a high fructose corn syrup having a target proportion of fructose, and the raffinate stream is converted to a fructose-enriched mixture using a glucose isomerase column, the linear program model may be used to minimize total costs incident to: replacing the glucose isomerase column as affected by the determined proportions of fructose and glucose in the fructose-enriched mixture; the frequency of replacing the cation resin in the SMB apparatus; removal of output stream of either or both of the SMB apparatus and glucose isomerase column; and maximizing production of the target high fructose corn syrup product per unit of cost.

The columns of the SMB apparatus may be loaded with any suitable adsorbent to separate the desired component from the other components of the input feed, as can be readily determined by one of ordinary skill in the art. In embodiments for enriching sugar syrups as illustrated herein for HFCSs the columns are loaded with a cation exchange resin such as sulfonic acid resin preferably in calcium form. The method of the present invention is suitable for use with any type of SMB system or configuration, including, but not limited to CSEP, ADSEP, ISMB and SSMB.

The method of the present invention eliminates most of the dilution caused by the eluent feed by utilizing an eluent containing the desired component. This creates value in reduced water costs and saves energy in reducing the energy required to evaporate the extract product to a higher dissolved solids concentration. Further, in the embodiment wherein the raffinate stream is recycled to the input feed or eluent feed, the method recovers most, or nearly all, of the fructose from the input stream so it becomes commercially acceptable to use the SMB system to effect an otherwise high loss separation technique, because the fructose that would otherwise be lost is actually completely recovered.

The process can be used to enrich the relative percentage of a higher value component of any mixture where the higher valued component can be chromatographically enriched relative to the lower value component and where it is desired to do so without substantial dilution of dissolved solids content the final product mixture in comparison to the input mixture. The yield, dissolved solids concentration and dilution of the final product will depend only on the limits of dissolved solid concentration necessary to effect a separation and the relative mobility of the higher value component to the lower value component over the solid phase of the chromatographic system.

Certain exemplary embodiments of the present invention are illustrated by the following non-limiting examples.

Example 1

The method of the present invention was performed using an 8-column standard laboratory scale SMB system from Semba Biosciences (Wisconsin USA) filled with a UBK555-Ca resin available for example from Johnson Matthey Co. (New Jersey, USA). A number of experiments were run at different input rates calculated to mimic the percentage of the feed rate applied to SMB resins actually used to enrich HFCS to 90% in a commercial plant. Thus, 135% plant resin utilization means the experiment was run at a total flow rate (i.e., the rate of flow of the combined input streams per bed volume) that is 35% greater than the flow rate per bed volume typically used to produce a 90% fructose syrup and 200% plant utilization means the flow rate was twice as fast as typical. The experiments were done with or without raffinate reload or with 42% fructose syrup added with water to the eluent. Reload means that a portion of the raffinate stream was recirculated back onto the SMB at a column position within the raffinate zone after the main raffinate stream is collected, for example at column position 12 in FIGS. 2 and 3. This is done to increase the dissolved solids concentration of the collected raffinate.

Figure 4:
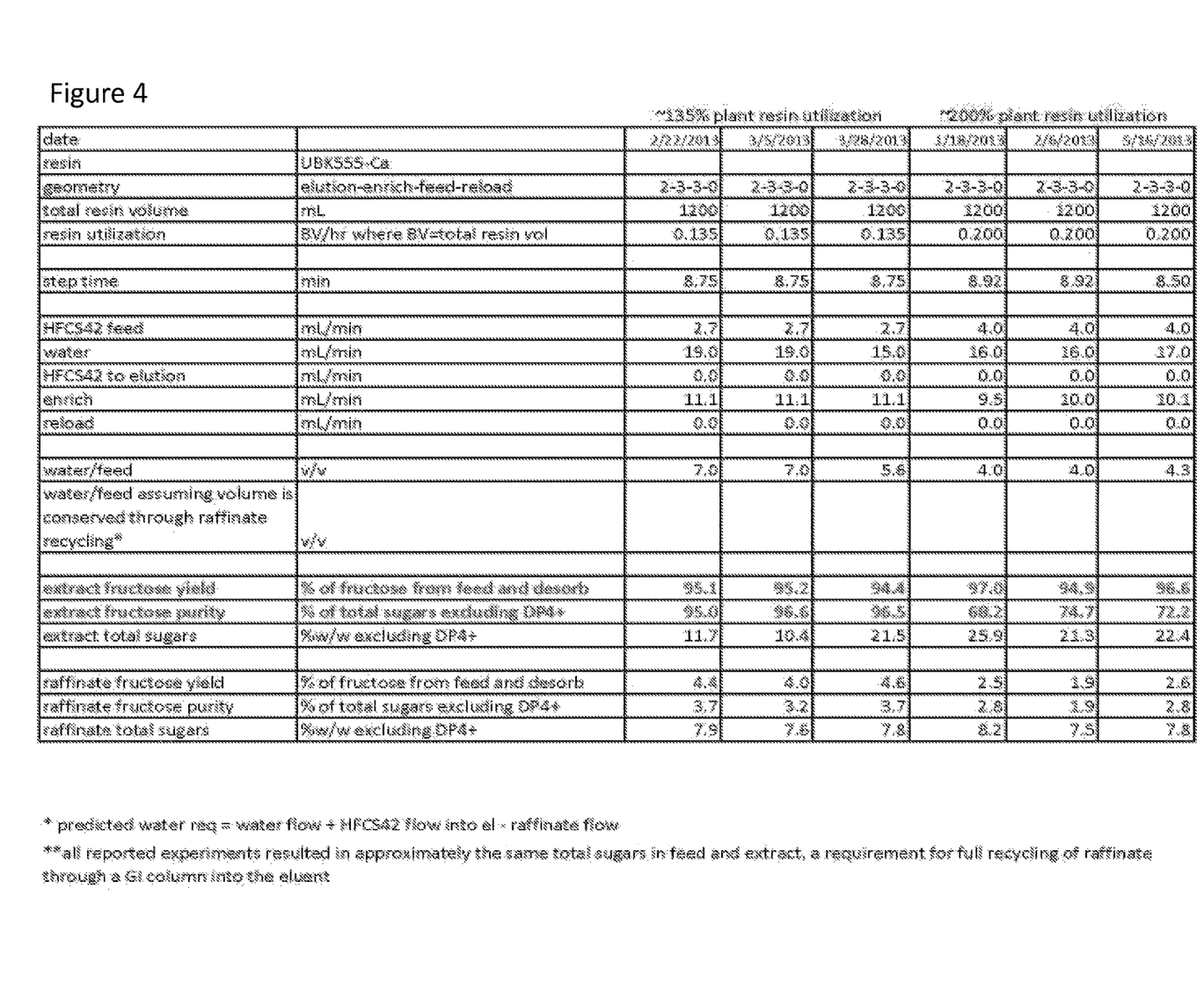
FIG. 4 is a table disclosing the results of an experiment for a conventional production of a highly enriched fructose syrup using water as the eluent as described in Example 1.
Figure 5:
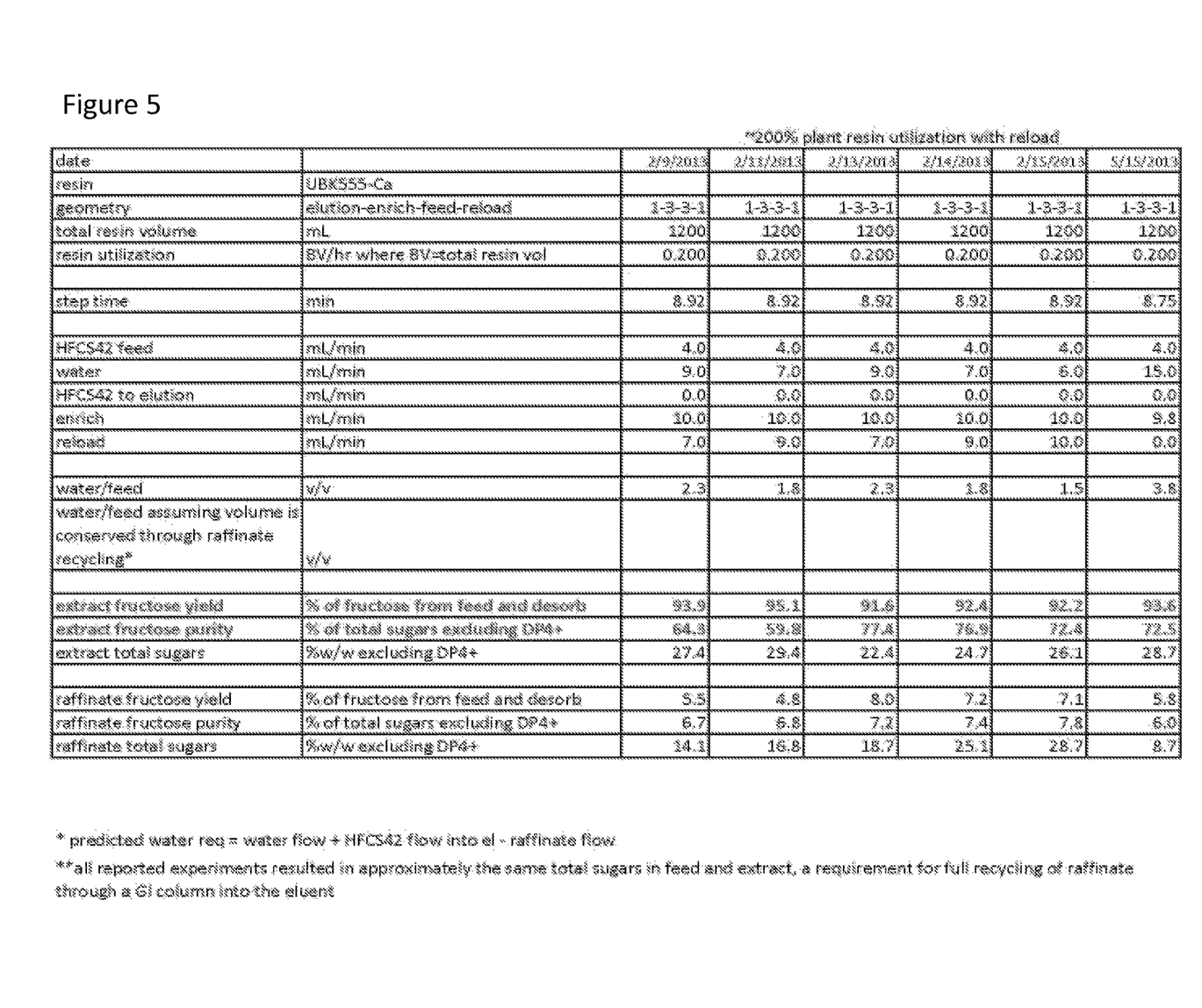
FIG. 5 is a table disclosing the results of an experiment for a conventional production of a highly enriched fructose syrup using water mixed with a reload of the raffinate as described in Example 1.
Figure 6:
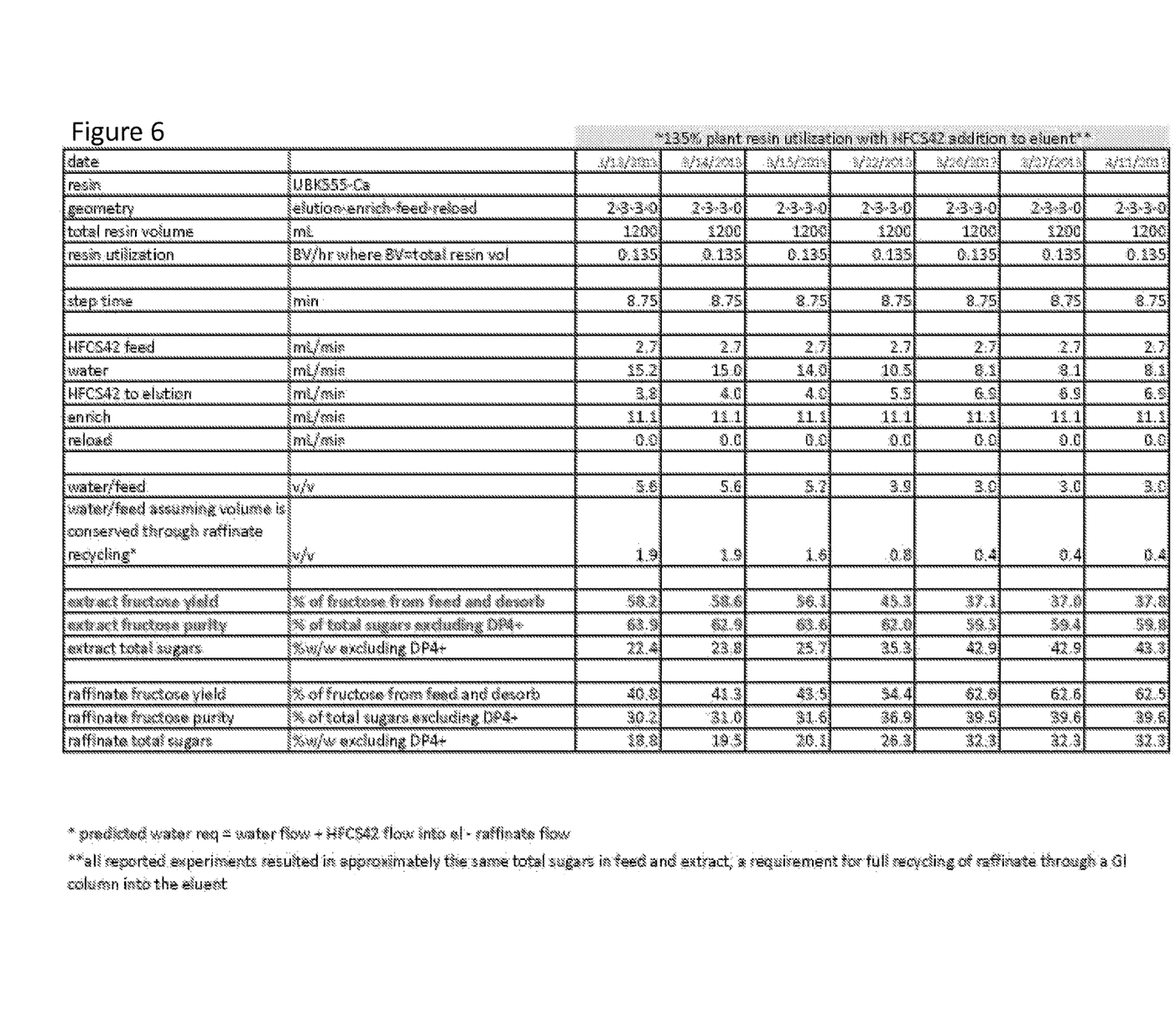
FIG. 6 is a table disclosing the results of experiments adding 42% fructose syrup to the eluent feed (row labeled "HFCS42 to elution") in addition to the water at a water to 42% fructose ratio ranging from 3.0 to 5.6 as described in Example 1.

The operating parameters for each experiment are detailed in FIGS. 4-6. FIGS. 4 and 5 show results of conventional production of a highly enriched fructose syrup using water as the eluent (FIG. 4) or water mixed with a reload of the raffinate (FIG. 5) which in both cases produced a syrup containing greater than 90% fructose with a dissolved solids content from roughly 10% to roughly 30% depending on whether or not there was reload of raffinate into the eluent stream. In each case, the input feed was 42% fructose syrup (row labeled "HFCS42 feed") having a dissolved solids content of about 60%.

FIG. 6 shows the results of experiments adding 42% fructose syrup to the eluent feed (row labeled "HFCS42 to elution") in addition to the water at a water to 42% fructose ratio ranging from 3.0 to 5.6. The row labeled "Extract fructose purity" shows the fructose syrup obtained from the elution zone in each extract product, which ranged from 59.4 to 63.9% fructose at a dissolved solids content ranging from 22.4% to 43.3%, which given the input feed had a dissolved solids content of 60% corresponds to a dissolved solids ratio of the eluent to input feed of 0.37 to 0.72.

Example 2

Figure 7:
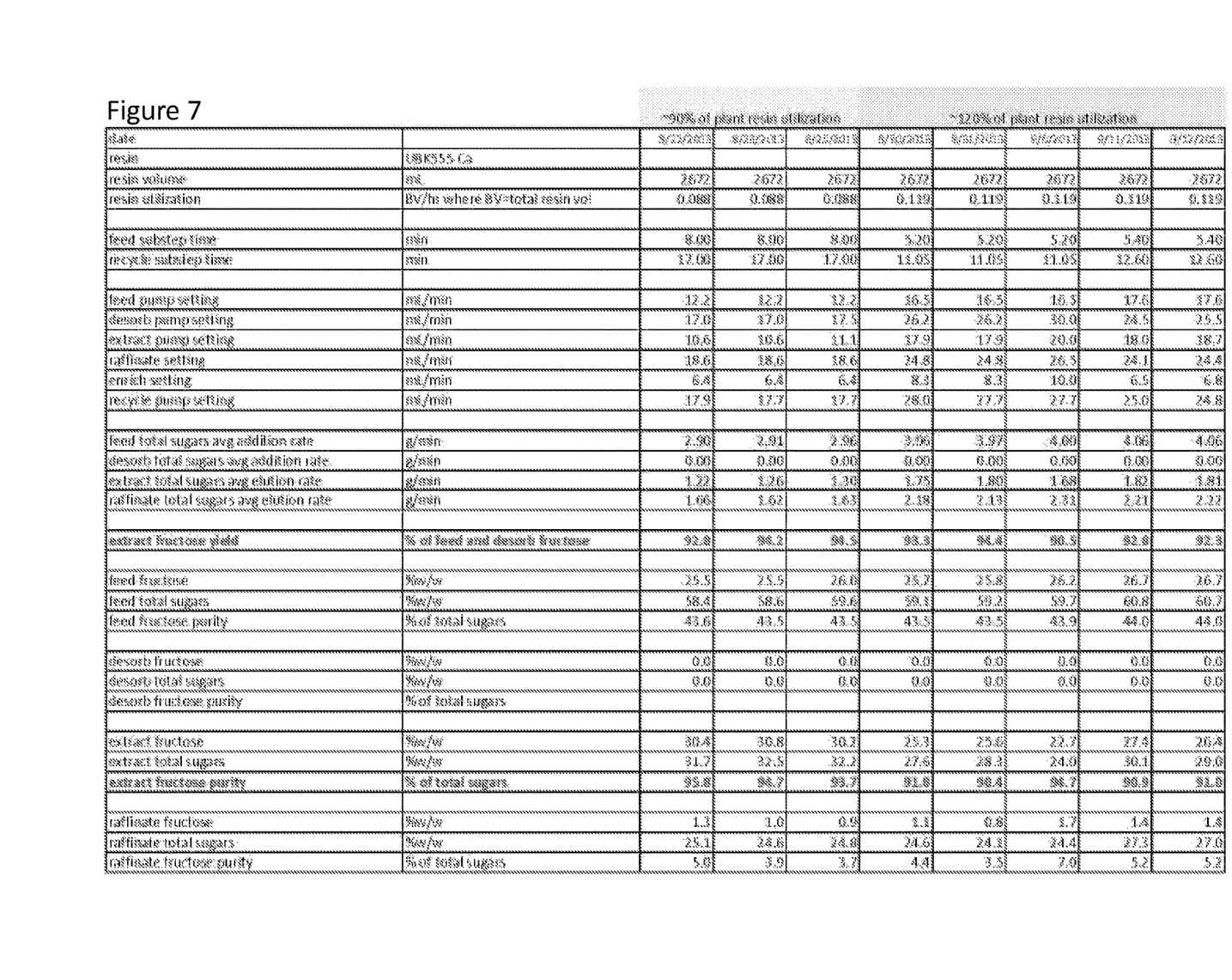
FIG. 7 is a table disclosing the results of an experiment from Example 2 using water alone as the eluent.

The method described in Example 1 was modified using 90% plant resin utilization and 120% plant resin utilization using water alone as the eluent (FIG. 7) or with 120% plant resin utilization with 42% fructose syrup added to the eluent. The operating parameters for each experiment are detailed in FIGS. 7 and 8. In each case, the input feed was 42% fructose syrup and the eluent feed comprised water only (FIG. 7) or water mixed with 42% syrup (FIG. 8). With water as the only eluent, the extract product was again a fructose syrup of greater than 90% with a dissolved solids content ranging from 24%-32.5%. When the 42% syrup was used a fructose syrup was extracted from the elution zone having a fructose content that ranged from 55.7% to 59.3% fructose (row labeled "extract fructose purity") at a dissolved solids content that ranged from 48% to 50.9% (row labeled "extract total sugars") which given the input feed had a dissolved solids content of 60% corresponds to a dissolved solids ratio of the eluent to input feed of 0.80 to 0.84.

Example 3

The method of the present invention was performed using a 12-column carousel laboratory scale SMB filled with a Dowex 99 Ca resin (310 mL total volume. The carousel had two outlets, extract 30 (product) and raffinate 32 (by-product), and two inlets, feed 16 and eluent 26. A 55-60% sugar syrup (42-44% fructose, dry basis) was pumped at 8 mL/min into the feed zone 16. The eluent had two pumps: one pump introduced the feed syrup at 11.7 mL/min into the eluent 26, for the first 33% of each step time, and a second pump delivered water into the same zone for the remainder of the step at 14.5 ml/min 38. The extract contained 37.8% sugars (67.2% fructose, dry basis). The raffinate contained 26.1% sugars (9.6% fructose, dry basis).

Only 10 of the 12 columns were used in the chromatography. The experiment was done with two eluent pumps connected to a computer and programmed to perform a feed-water pulse. At a set time in the step the computer would shut off the pump introducing 42% fructose in to the elution zone and turn on the water pump. The water would continue to be introduced to the elution zone for the rest of the step. Once the step movement occurred (or the SMB rotated) the computer would shut the water pump off and turn back on the 42 fructose pump.

Figure 10:
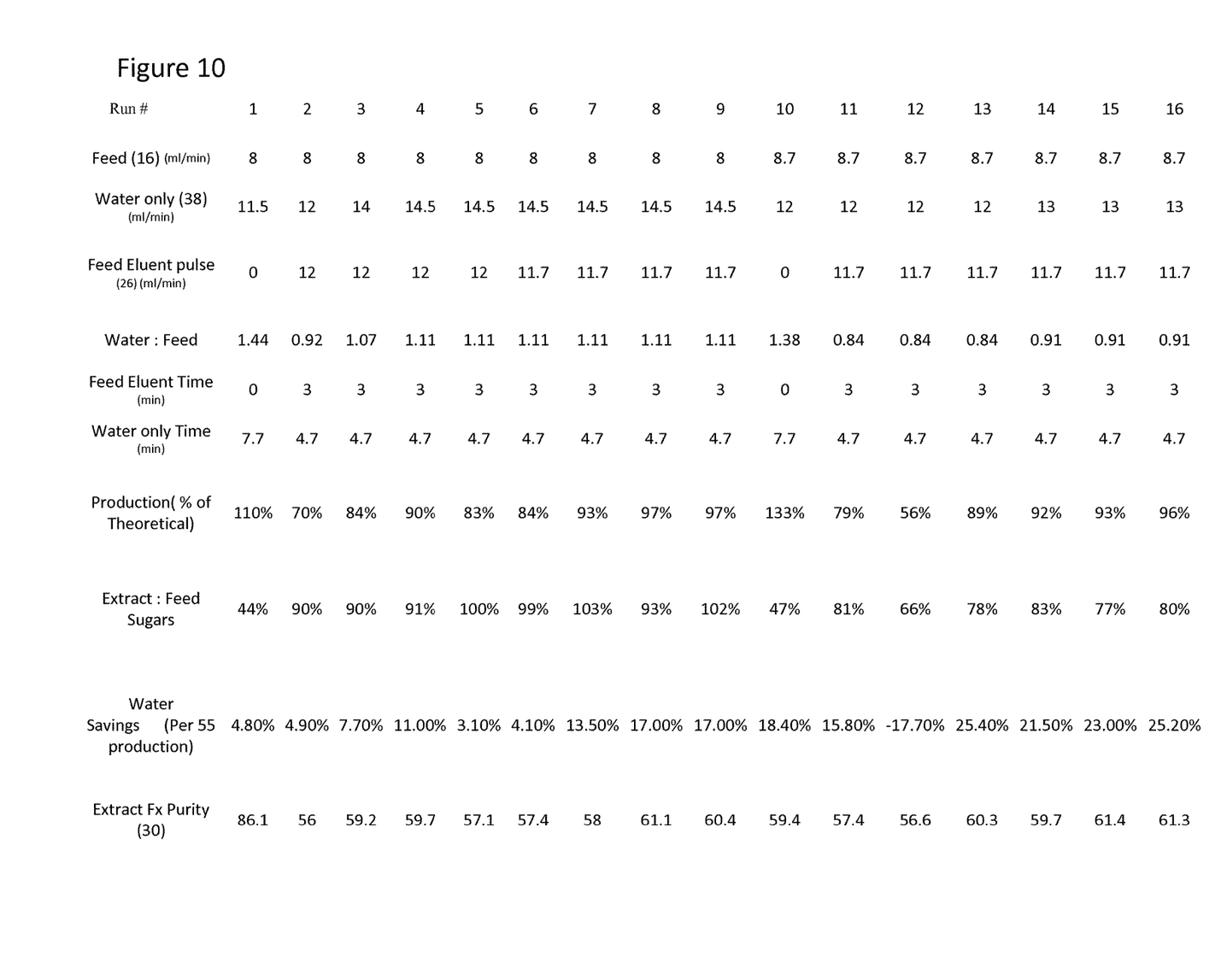
FIG. 10 is a table disclosing the results of the experiment from Example 3 using a feed-water pulse as the eluent.

The operating parameters for each experiment are detailed in FIG. 10. The row labeled Feed Time (min) shows the amount of time 42 fructose was pumped into the elution zone. The row labeled Water Time (min) shows the amount of time water was pumped into the elution zone. The row labeled Water:Feed shows the relationship of the total amount of water put into the system at the elution zone 28 compared to the feed put in to the feed zone 18. For example, in column 4, for every gallon of feed that was put into the feed zone, 1.11 gallons of water was put into the elution zone. Effectiveness was determined by calculated percent of production of plant and water savings per 55 production.

The elution feed time as ran in this experiment is 38.9% of the total step time, therefore the water feed time was (100-38.9=) 61.1%. The control (column 3 of the table in FIG. 10) ran at a 33% increased feed rate from theoretical, which is necessary to maintain theoretical maximum production. Column 9 shows the ability of this system to hit the production values required while decreasing the total water used by 17%. The feed eluent pulse can be altered so that the total amount of dry solids in the feed eluent is equal to the raffinate dry solids over a total step movement. This configuration avoids having to blend water and feed eluent (26) as depicted in FIG. 2 and allows for a pulse of water to displace the sugars off of the resins which allows for a higher recovery.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed is:

1. A method of adjusting the composition of a chromatography product to achieve a target proportion of a desired component, comprising:
   contacting an input zone of a simulated moving bed ("SMB") chromatography apparatus comprising a cation resin with an input feed comprising input feed proportions of the desired component and a second component and having an input feed dissolved solids content;
   contacting an elution zone of the SMB apparatus with an eluent feed comprising eluent feed proportions of the desired component and the second component and having an eluent feed dissolved solids content; and
   operating the SMB apparatus to blend the desired component from the input feed, delivered through an enrichment zone of the SMB apparatus, with the desired component from the eluent feed, delivered though the elution zone, to form an extract product comprising the target proportion of the desired component and an extract dissolved solids content,
      wherein the target proportion of the desired component is greater than the input feed proportion of the desired component, and
      wherein the extract dissolved solids content is at least 50% of the input feed dissolved solids content; and
   collecting the extract product having the target proportion of the desired component from the SMB apparatus;
   wherein the eluent feed proportion of the desired component is greater than the input feed proportion of the desired component.

2. The method of claim 1, wherein said eluent feed proportion of the desired component is selected to blend with the desired component from the input feed delivered through the enrichment zone to result in the target proportion of the desired component in the extract product.

3. The method of claim 1 wherein a volume of the eluent feed is diluted by no more than 0.2 volumes of water as compared to the effluent feed volume prior to contacting the elution zone.

4. The method of claim 1, wherein the eluent feed is continuously combined with water to contact the elution zone with a diluted eluent feed, wherein a volume ratio of eluent feed to water is 1:2.

5. The method of claim 1 wherein the eluent feed is contacting the elution zone for a period of time, followed by a second period of time where water is contacting the elution zone without the eluent feed, wherein the first period of time and the second period of time are selected so that a volume ratio of eluent feed to water is 1:2 prior to a step movement in the SMB apparatus.

6. The method of claim 1, further comprising collecting from the SMB apparatus a raffinate stream having raffinate proportions of said desired component and said second component, wherein the raffinate proportion of said second component is higher than the input feed proportion of the second component.

7. The method of claim 1 wherein said desired component is fructose and said second component is glucose.

8. The method of claim 6 wherein said desired component is fructose and said second component is glucose and further comprising:
   adding the raffinate stream to a input stream comprising glucose to form a combined glucose-enriched stream;
   contacting a glucose isomerase chromatography column comprising glucose isomerase with the combined glucose enriched stream for a time sufficient to enrich a fructose proportion in the column; and
   eluting from the glucose isomerase column a fructose-enriched mixture.

9. The method of claim 8 wherein the step of contacting the input zone with the input feed comprises contacting the input zone with the eluted fructose-enriched mixture.

10. The method of claim 8 wherein said step of contacting the glucose isomerase column comprises contacting the column for less than a time required to bring the proportions of fructose and glucose to an equilibrium point for the glucose isomerase, whereby the eluted fructose-enriched mixture has a lower fructose proportion than would be obtained by contacting the glucose isomerase column for the time required to bring the proportions of fructose and glucose to the equilibrium point for the glucose isomerase.

11. The method of claim 10 wherein the step of contacting the input zone with the input feed comprises contacting the input zone with the eluted fructose-enriched mixture.

12. The method of claim 1 wherein no water is added to the SMB apparatus that would dilute the extract dissolved solids content in comparison to the input feed dissolved solids content.

13. The method of claim 1 wherein said desired component is fructose and said second component is glucose, wherein the input feed proportion of fructose is 42-44%, with the remainder being glucose, and target proportion of fructose in the extract product is 55%-60%, with the remainder being primarily glucose.

14. The method of claim 13 wherein the input feed dissolved solids content and the extract dissolved solids content are each at least 50% wt/vol.

15. The method of claim 1, wherein the extract dissolved solids content is at least 60% of the input feed dissolved solids content.

16. The method of claim 1, wherein the extract dissolved solids content is at least 80% of the input feed dissolved solids content.

17. A method of adjusting the proportion of fructose in a high fructose corn syrup product to achieve a target proportion of said fructose, comprising:
   contacting a simulated moving bed ("SMB") chromatography apparatus containing a cation resin that facilitates enrichment of fructose over glucose in a fructose enrichment zone of the SMB apparatus with an input feed and an eluent feed, wherein each of said input feed and said eluent feed comprises mixtures of fructose and glucose and has a dissolved solids content;
   operating the SMB apparatus to produce in the fructose enrichment zone the high fructose corn syrup product having the target proportion of fructose and a product dissolved solids content; and
   collecting from the fructose enrichment zone of the SMB apparatus the high fructose corn syrup product having the target proportion of fructose,
      wherein the high fructose corn syrup product has a dissolved solids content that is at least 50% of the dissolved solids content of the input feed.

18. The method of claim 17, wherein the high fructose corn syrup product has a dissolved solids content that is at least 60% of the dissolved solids content of the input feed.

19. A method of optimizing operational costs of producing a high fructose corn syrup product having a target proportion of fructose, comprising:
   operating a simulated moving bed ("SMB") apparatus to achieve the target proportion of fructose according to the method of claim 13;
   collecting a glucose-enriched raffinate stream from the SMB apparatus wherein a glucose proportion in said raffinate stream is higher than a glucose proportion in said input feed;
   using the glucose-enriched raffinate stream as an input stream for a glucose isomerase column;
   operating the glucose isomerase column to convert glucose in the input stream to fructose to produce a fructose-enriched mixture having determined proportions of fructose and glucose, wherein said input feed of said contacting step comprises the fructose-enriched mixture; and
   using a linear program model to minimize the total costs incident to:
   (a) replacing the glucose isomerase column as affected by the determined proportions of fructose to glucose in the fructose-enriched mixture;
   (b) frequency of replacing the cation resin in the SMB apparatus;
   (c) removal of water from an output stream of either of both of the SMB apparatus and glucose isomerase column; and
   (d) maximizing production of the target high fructose corn syrup product per unit of cost.

* * * * *